(12) United States Patent
Reiley

(10) Patent No.: US 8,361,003 B2
(45) Date of Patent: Jan. 29, 2013

(54) SYSTEMS, DEVICES, AND METHODS FOR DIAGNOSING AND TREATING CONDITIONS OF THE SPINE

(75) Inventor: Mark A Reiley, Berkeley, CA (US)

(73) Assignee: Si-Bone, Inc., San Jose, CA (US)

( * ) Notice: Subject to any disclaimer, the term of this patent is extended or adjusted under 35 U.S.C. 154(b) by 158 days.

(21) Appl. No.: 12/584,163

(22) Filed: Sep. 1, 2009

(65) Prior Publication Data

US 2011/0054373 A1    Mar. 3, 2011

(51) Int. Cl.
*A61F 5/00* (2006.01)
*A61F 5/37* (2006.01)
*A61F 5/02* (2006.01)
*A61B 19/00* (2006.01)
*A61B 5/103* (2006.01)

(52) U.S. Cl. .......... 602/19; 128/869; 128/874; 600/594; 2/44

(58) Field of Classification Search ............. 602/19, 602/20, 32, 36, 5–6, 13; 128/845, 846, 847, 128/869, 870, 873, 874, 875, 897, 898; 280/15; 482/54, 69; 600/594–595, 534–536; 2/44
See application file for complete search history.

(56) References Cited

U.S. PATENT DOCUMENTS

| 5,599,286 | A * | 2/1997 | Labelle et al. ............... 602/19 |
| 2005/0067816 | A1 | 3/2005 | Buckman |
| 2006/0161087 | A1* | 7/2006 | Carter et al. .................. 602/32 |
| 2007/0167897 | A1* | 7/2007 | Schock ........................ 602/32 |

OTHER PUBLICATIONS

International Search Report and Written Opinion of the International Searching Authority; PCT/US2010/002379; Oct. 25, 2010.

* cited by examiner

*Primary Examiner* — Kevin C Sirmons
*Assistant Examiner* — Ophelia A Hawthorne
(74) *Attorney, Agent, or Firm* — Shay Glenn LLP

(57) ABSTRACT

Systems, devices, and methods for diagnosing and treating conditions of the spine employ a garment for selectively positioning vertebrae of a spine of a supine individual, e.g., during diagnostic imaging of the spine. The garment affects movement of vertebrae that can be diagnostically correlated with incidents of back pain.

10 Claims, 14 Drawing Sheets

SYSTEMS, DEVICES, AND METHODS FOR DIAGNOSING AND TREATING CONDITIONS OF THE SPINE

FIELD OF THE INVENTION

The invention generally relates to systems, devices, and methods for diagnosing and treating conditions of the spine, including systems, devices, and methods for positioning the spine while obtaining diagnostic images.

BACKGROUND OF THE INVENTION

Many different conditions may cause back pain. Doctors can use several tests to visualize the spine to get an idea of what might be causing the back pain. The imaging diagnostic procedures that are currently used to image the spine include plain x-rays, myelograms, bending X-rays, PET scans, CT scans, CT myelograms, MRI scans, MRI's with contrast, and discograms.

No single test is perfect in that it identifies the absence or presence of disease 100% of the time. The problem exists that it is not always possible to obtain a correct diagnosis of the cause of a patient's back pain through state of the art imaging.

SUMMARY OF THE INVENTION

The inventor has discovered that part of the failure to diagnose back pain through imaging is that, when the imaging study is performed, the patient is typically in a position in which there is no back pain. Thus, whatever is causing the patient's back pain will not be observed.

The present invention overcomes this problem. The invention makes possible precise positional adjustments to the patient's spine and pelvic bones during imaging to move the patient spine into a position that causes pain. The spine position and the incidence of pain can be correlated to yield a diagnosis as to the underlying cause of the back pain.

The invention provides systems, devices, and methods for diagnosing back pain that include a garment for selectively positioning vertebrae of a spine of a supine individual during diagnostic imaging of the spine. The garment affects movement of vertebrae that can be diagnostically imaged and correlated with incidents of back pain.

The garment can also be used as a diagnostic tool in and of itself, without the use of imaging.

Other objects, advantages, and embodiments of the invention are set forth in part in the description which follows, and in part, will be obvious from this description, or may be learned from the practice of the invention.

DESCRIPTION OF THE PREFERRED EMBODIMENT

A. The Spine

Figure 1:
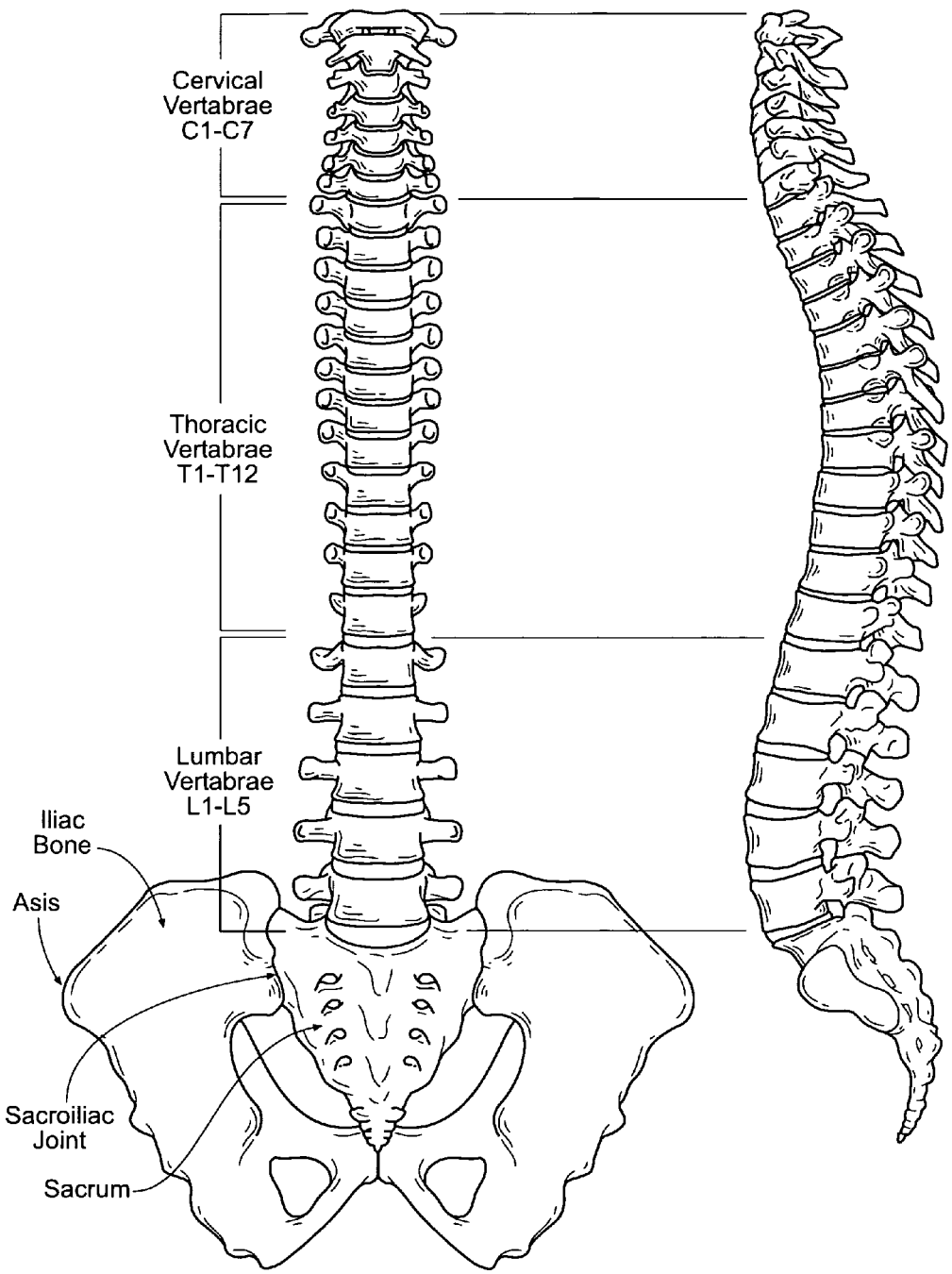
FIG. 1 is an anatomic view of a human spine, showing the cervical, thoracic, lumbar, and sacral regions of vertebrae.

FIG. 1 shows a human spinal column, also called the spine, or backbone. The spine is a flexible column extending from neck to pelvis, made of a series of bones, called the vertebrae. The major function of the spine is protection of the spinal cord. It also provides stiffening for the body and attachment for the pectoral and pelvic girdles and many muscles. In humans, an additional function is to transmit body weight during walking and standing.

In humans (and other mammals), the spine includes four main regions: (1) the cervical, in the neck, with articulates with the head; (2) the thoracic, in the chest, which articulates with the ribs; (3) the lumbar, in the lower back, which articulates with bending and stretching; and (4) the sacrum, which articulates with the pelvic girdle at the sacroiliac joint.

As shown in FIG. 1, humans have 7 cervical vertebrae (numbered C1 to C7), 12 thoracic vertebrae (numbered T-1 to T-12), five 5 lumbar vertebrae (numbered L-1 to L-5), and 5 fused sacral vertebrae.

Figure 2:
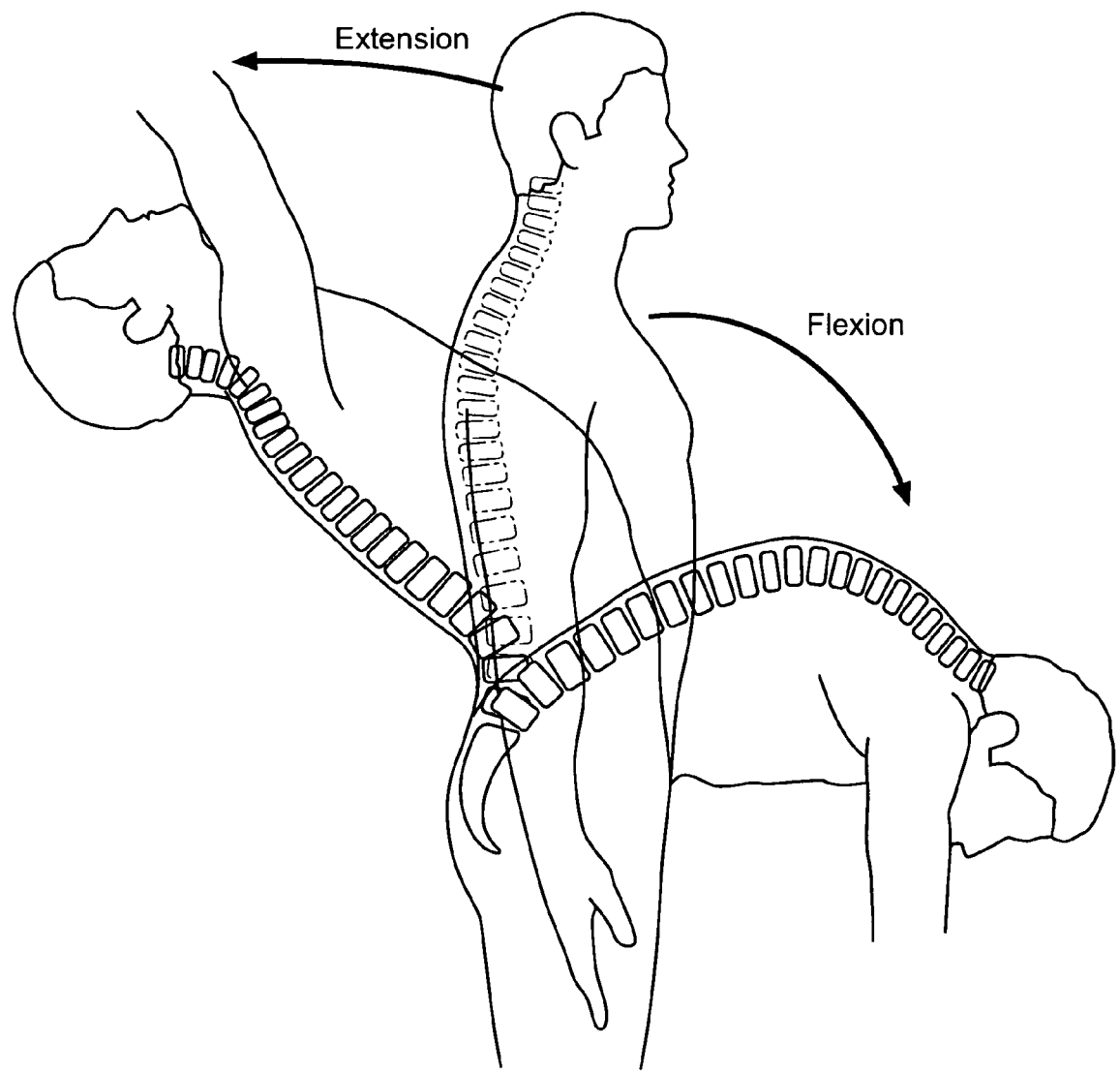
FIG. 2 shows the spine in conditions of extension and flexion.

As shown in FIG. 2, when an individual bends backward, the spine is said to be in "extension." When an individual bends forward, the spine is said to be in "flexion." Depending on the source of the back pain, back pain can occur during extension, or during flexion, or during both.

B. The Garment

FIGS. 3A to 3E and 4A to 4C show a garment 10 that embodies features of the invention. The garment 10 is made of durable fabric, rubber, or synthetic material (e.g., canvas or wet suit material) and is sized and configured to be worn by an individual. The material of the garment 10 is substantially transparent to the imaging energy; that is, it does not substantially interfere with the diagnostic imaging.

Figure 3A:
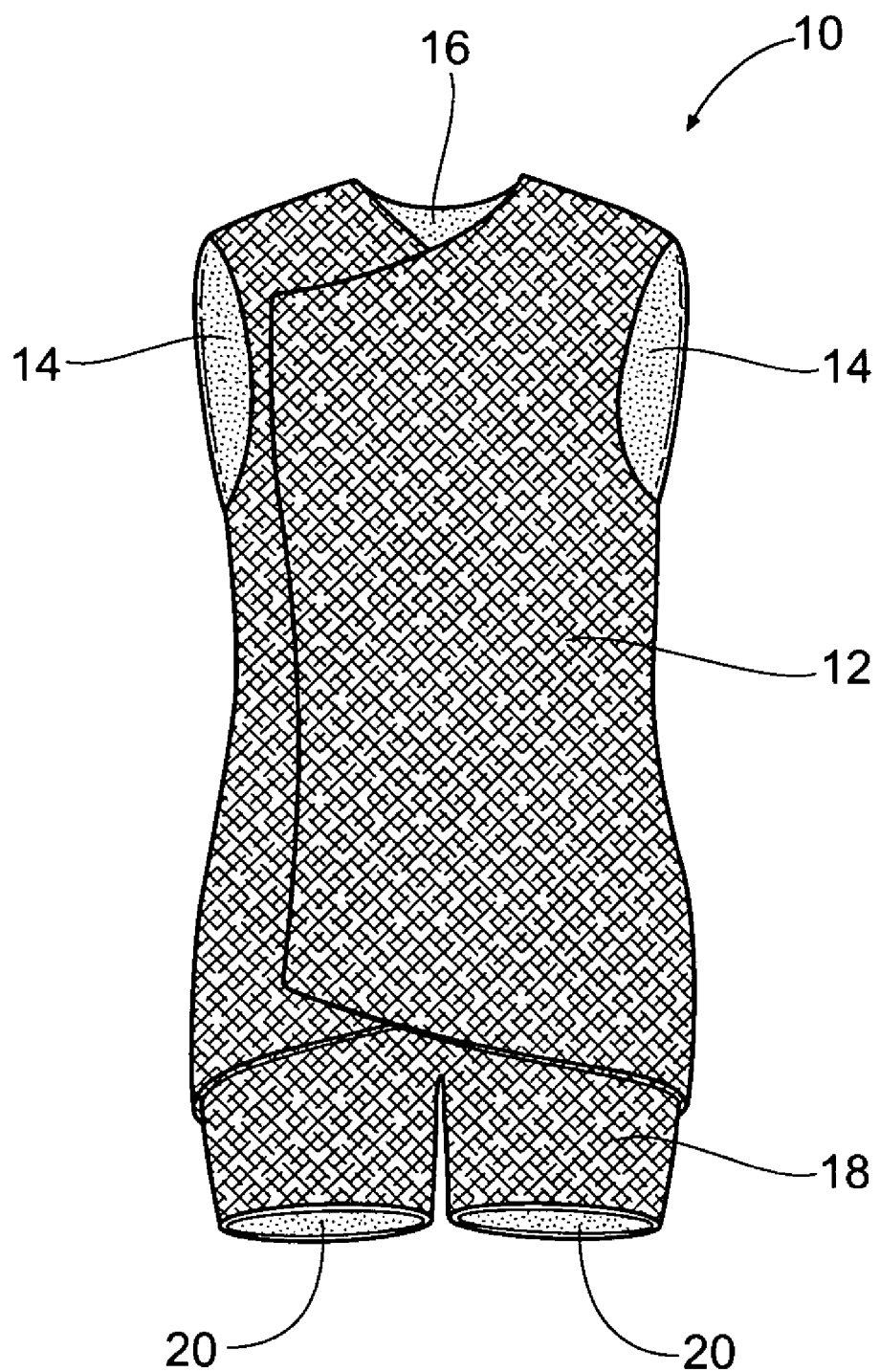
FIG. 3A is a front view of a garment for selectively positioning vertebrae of a spine of a supine individual during diagnostic imaging of the spine by affecting movement of vertebrae that can be diagnostically imaged and correlated with back pain, the garment being shown in a closed position.
Figure 4A:
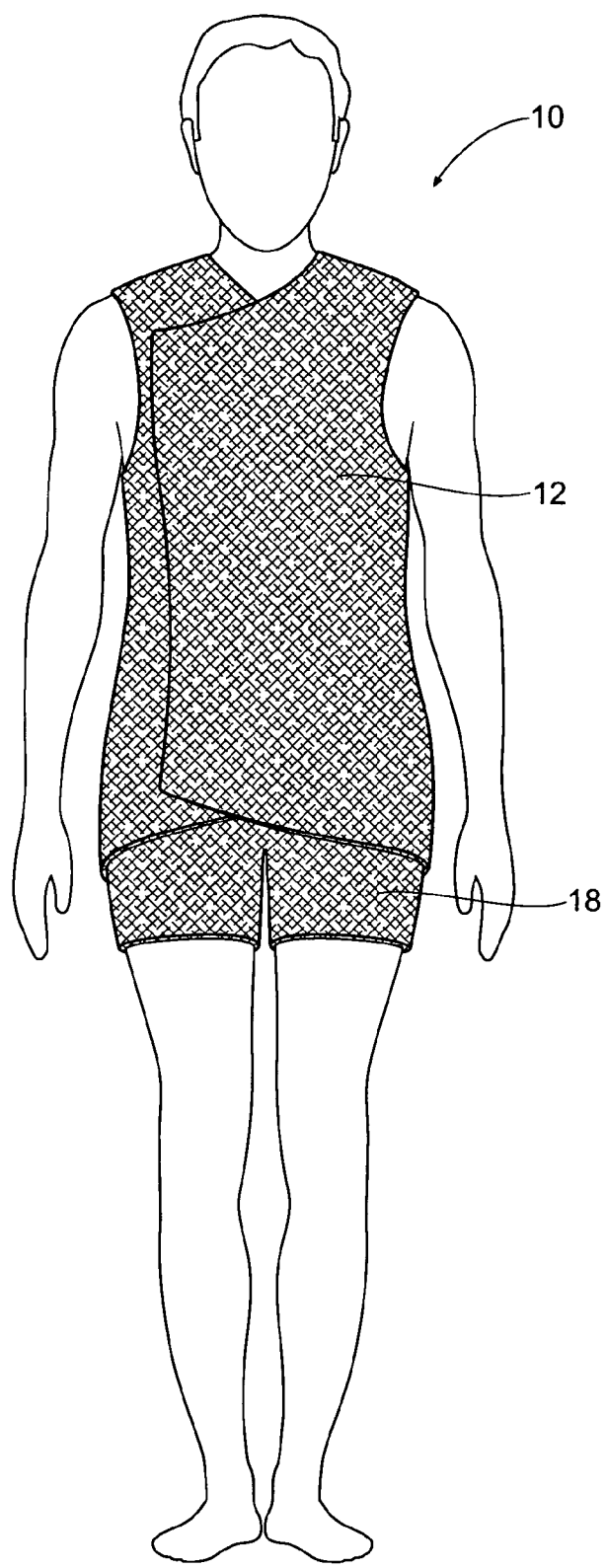
FIGS. 4A and 4B are, respectively, front and side views of the garment shown in FIG. 3A when worn by an individual.
Figure 4B:
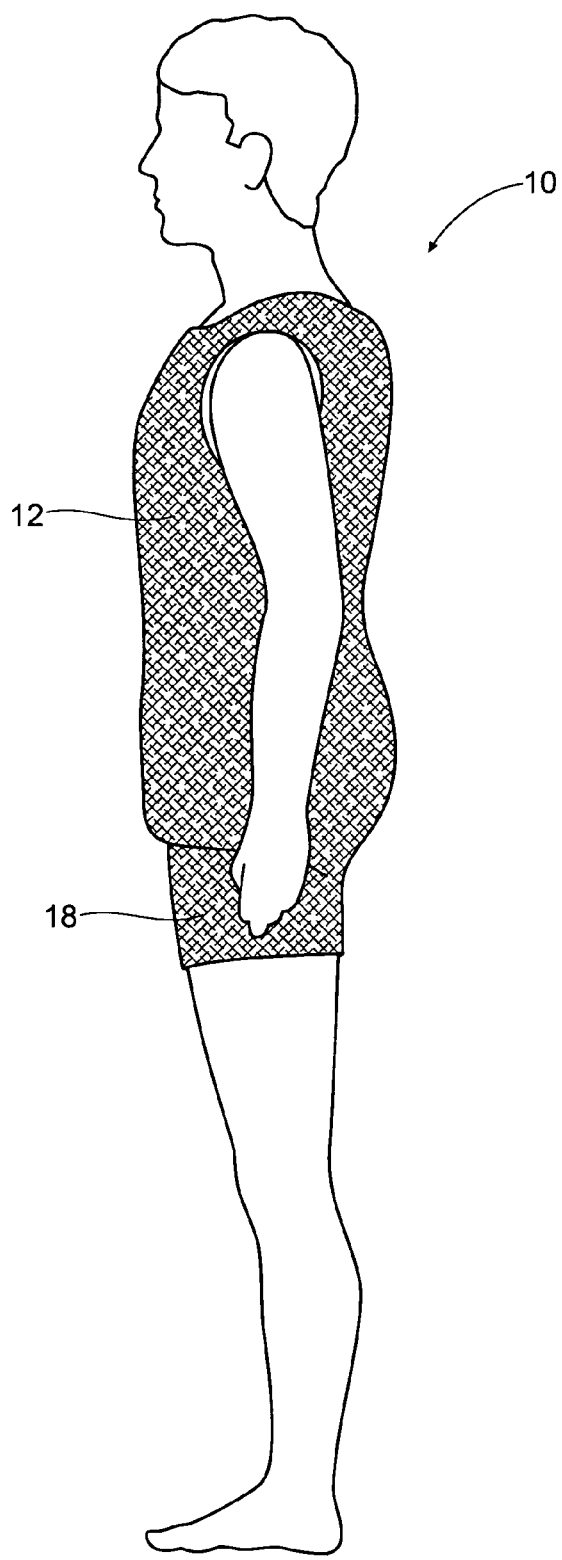

As shown in FIG. 3A, the garment 10 includes a vest region 12, with arm and neck openings 14 and 16, so that the vest region 12 can be comfortable worn on the upper torso, as FIGS. 4A and 4B show.

As shown in FIG. 3A, the garment 10 also desirably includes a pantaloon region 18, with leg openings 20, so that the pantaloon region 18 can be worn about the waist and hips like trousers, as FIGS. 4A and 4B show. In an alternative embodiment, the garment 10 can include only a vest region 12, with no pantaloon region 18.

Figure 3B:
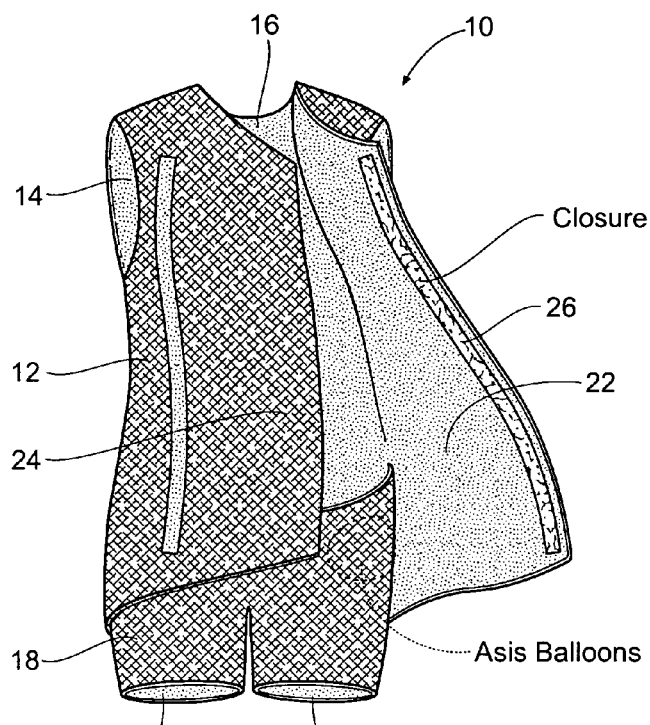
FIGS. 3B and 3C are front views of the garment shown in FIG. 3A, with the garment partially and fully opened, respectively, FIG. 3C further showing a series of expandable segments within the garment that are precisely positioned to align, when the garment is worn, with groups of vertebrae or individual vertebrae along the thoracic, lumbar, and sacral regions of the spine, as well as with pelvic bones affecting the sacroiliac joint.
Figure 3C:
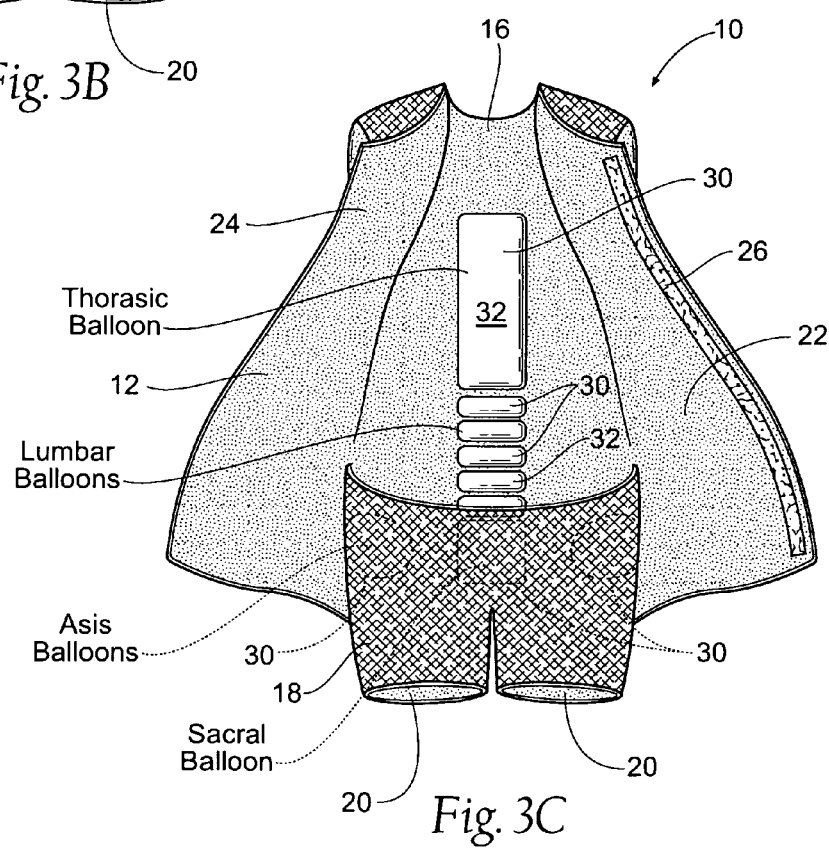
Figure 4C:
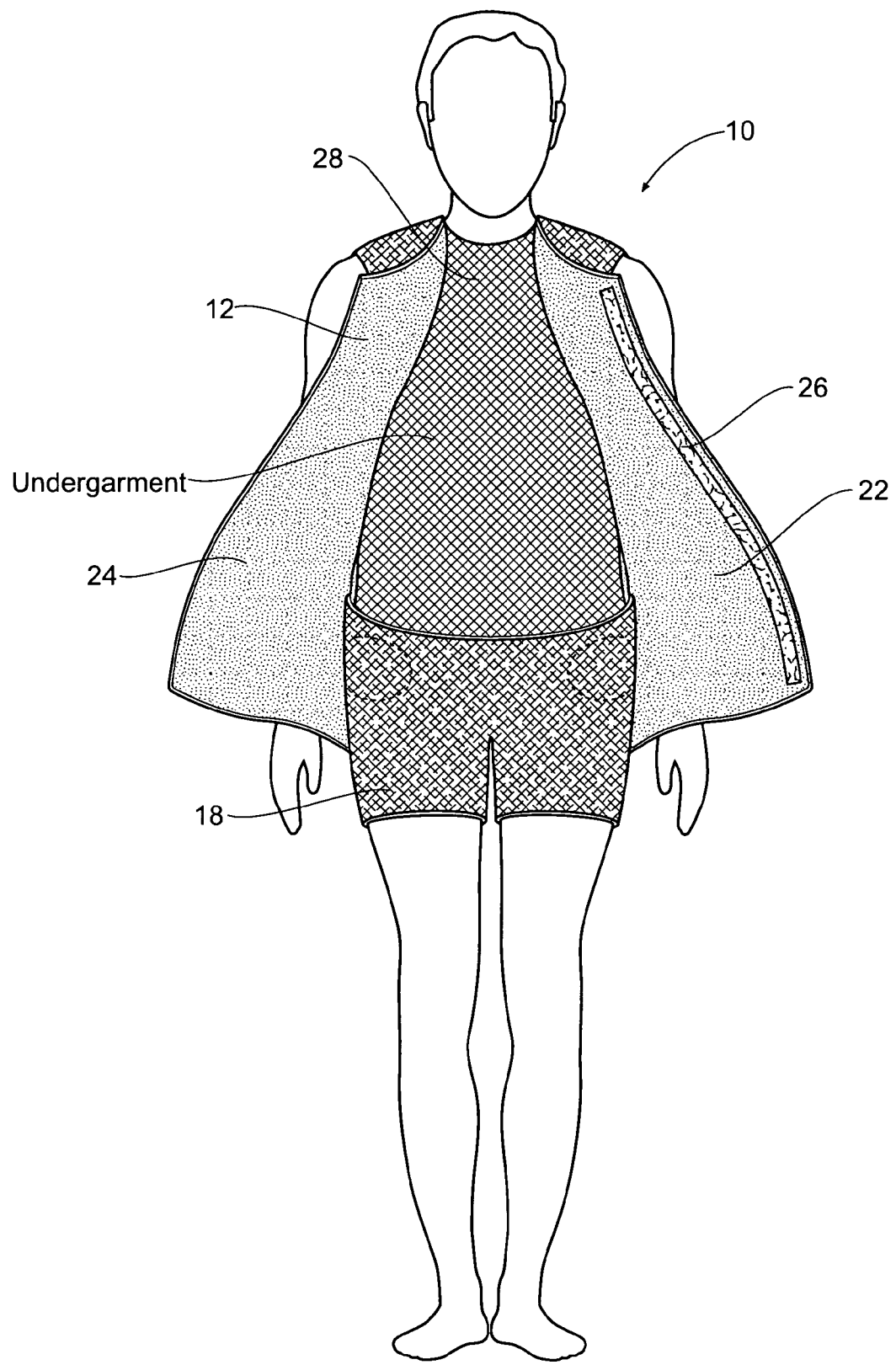
FIG. 4C is a front view of the garment shown in FIG. 3A, when in an open condition (as shown in FIG. 3C), further showing an undergarment that can be worn underneath the garment during use.

In the illustrated embodiment, see FIGS. 3B, 3C, and 4C, the vest region 12 includes overlapping left and right flaps 22 and 24 that open to allow a person to put the vest region 12 and pantaloon region 18 on. The left and right flaps 22 and 24 close in an overlapping condition (shown in FIG. 3A) to secure the vest region 12 on the upper torso and the pantaloon region 18 on the hips and waist (see FIGS. 4A and 4B show). A closure mechanism 26 is carried by one or both of the flaps 22 and 24 to releasably hold the flaps 22 and 24 in a closed condition. The closure mechanism 26 can comprise, e.g., VELCRO® material, plastic buttons, plastic hooks, or plastic snaps, made of materials which do not interfere with the imaging.

As shown in FIG. 4C, a disposable or nondisposable (but washable) inner garment 28 can be provided. The inner garment 28 keeps the main outer garment 10 from coming into direct contact with the skin of a patient, so the outer garment 10 can be used by multiple patients undergoing imaging. Like the garment 10 itself, the inner garment 28 is substantially transparent to the imaging energy so that it does not substantially interfere with the diagnostic imaging.

Figure 6:
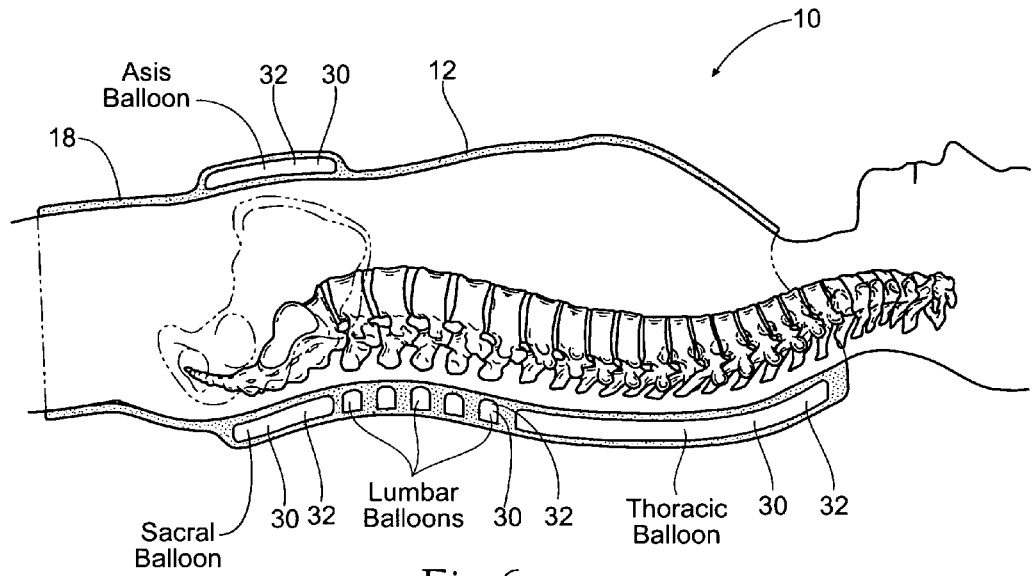
FIG. 6 is a side section view of the individual shown in FIG. 5, showing the alignment of the expandable sections with groups of vertebrae or individual vertebrae along the thoracic, lumbar, and sacral regions of the spine, as well as with pelvic bones affecting the sacroiliac joint, the expandable sections being in a normal collapsed, and not enlarged, condition.

As shown in FIG. 3C, the garment 10 includes a series of expandable segments 30. The expandable segments 30 are precisely positioned to align, when the garment 10 is worn, with groups of vertebrae or individual vertebrae along the thoracic, lumbar, and sacral regions of the spine, as well as with pelvic bones affecting the sacroiliac joint, as FIG. 6 shows.

Figure 5:
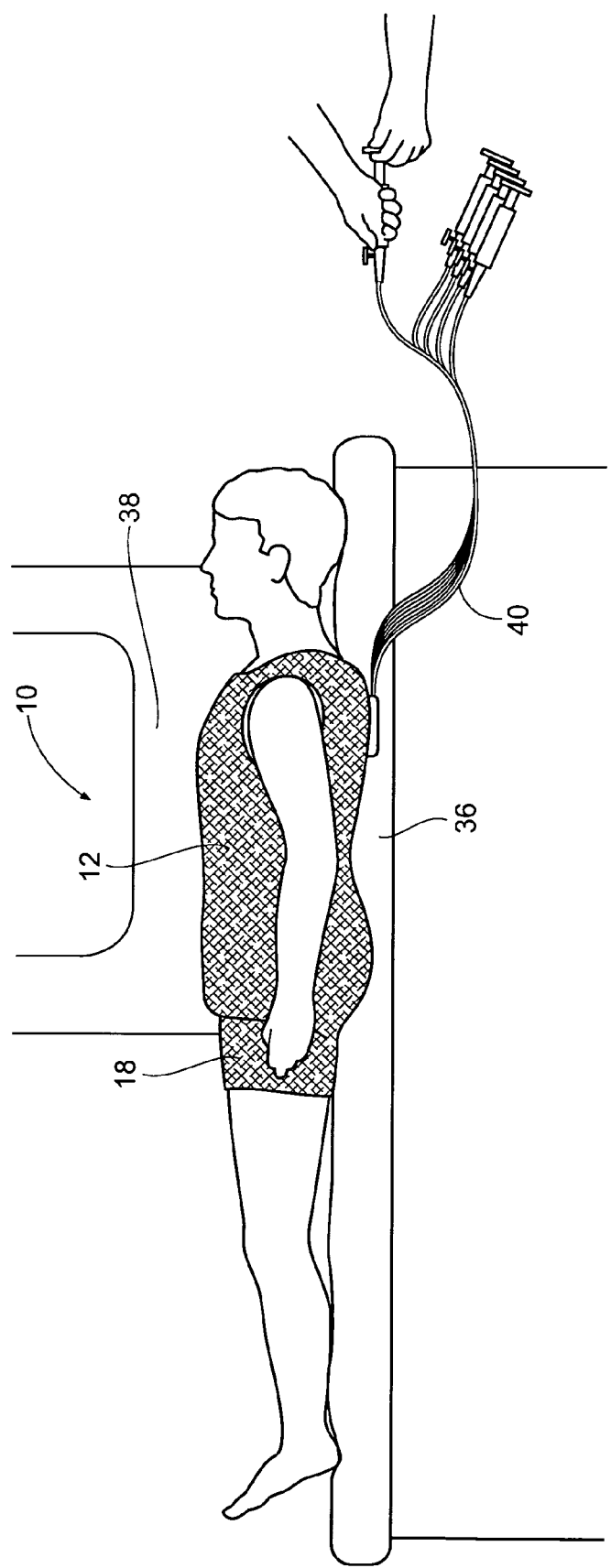
FIG. 5 is a view of the individual shown in FIG. 4A wearing the garment laying supine on a table in an imaging field.

The expandable segments 30 are made from material that assumes a normal lay-flat condition, as FIG. 5 shows, but can be enlarged or expanded into an enlarged condition that preferentially presses against the adjoining vertebrae. The material of the garment 10 is less flexible that the material of the expandable segments 30, so that, during enlargement, the expandable segments 30 expand preferentially inward into the interior of the garment 10. By pressing against the vertebrae, the expandable segments preferentially move alter the position of the vertebrae, muscles, and nerves to simulate extension and/or flexion and/or other orientation of the spine and pelvic region while the patient otherwise lays supine for imaging, as FIGS. 5 and 7 show.

The expandable segments 30 are made from a material that is substantially transparent to the imaging energy, so that it does not substantially interfere with the diagnostic imaging.

To affect preferential enlargement the expandable segments 30, the garment 10 further includes an array of actuators 32 that form or are otherwise carried within the expandable segments 30. The actuators 32 comprise structures that can be controllably enlarged, either by conveyance of liquid or air (either of which can be called a "fluid") or by mechanical means, from a normal collapsed condition to an enlarged, expanded condition. It is by operation of the actuators 30 that the expandable segments 30 enlarge to preferentially press against adjacent vertebrae or pelvic bone of the individual wearing the garment 10, moving and orientating vertebrae, muscles, and nerves of the spine. The actuators 32 are made from a material or materials that is/are substantially transparent to the imaging energy, so that the actuators 32 do not substantially interfere with the diagnostic imaging.

Figure 7:
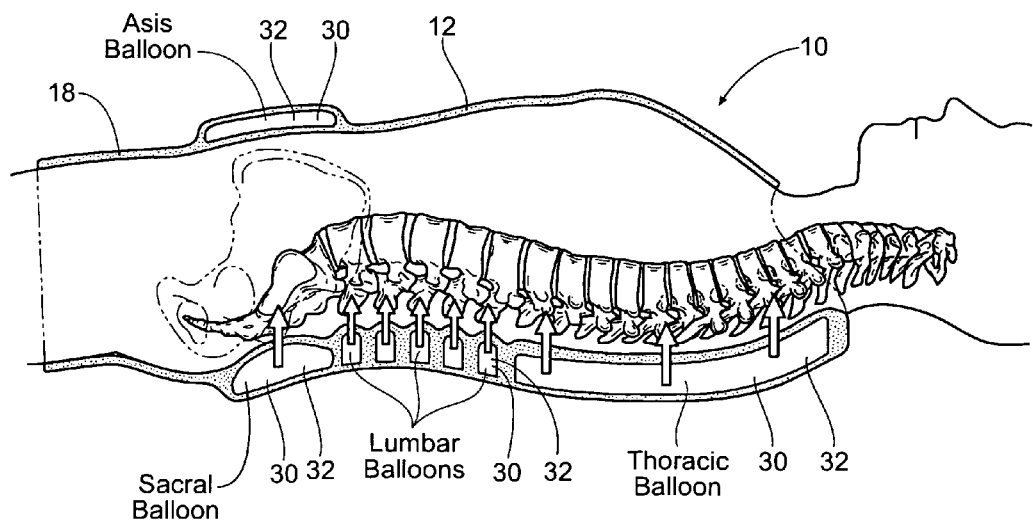
FIG. 7 is a side section view of the individual, like that shown in FIG. 6, but with all the expandable sections enlarged by fluid pressure to press against the vertebrae to affect movement of the vertebrae so that movement of the vertebrae can be diagnostically imaged.

While the individual wearing the garment 10 lays supine to undergo imaging (as FIGS. 5, 6, and 7 show), the actuators 32 are operated to apply coordinated external pressure to the vertebrae in regions of the spine. Operation of the actuators 32 affects predictable movements of the spine in desired directions, while imaging occurs, with the objective to cause an incident of back pain that can be coordinated with spine orientation and thereby lead to a diagnosis of the source of the back pain. That is, the incident of back pain can be correlated to an orientation of the spine that is captured by the imaging at the time the pain occurs. In this way, the orientation and motion of the spine that causes back pain can be systematically simulated and examined, to identify the particular bone or bones which are being moved to cause the back pain.

Figure 12:
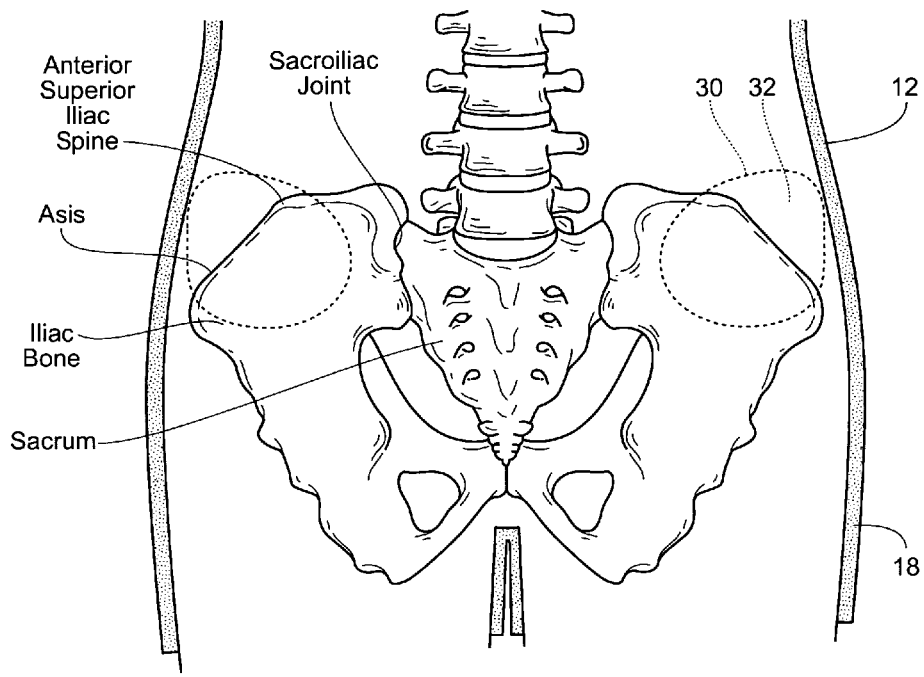
FIG. 12 is a front view of the individual shown in FIG. 4A, showing in greater detail the location of the expandable sections over opposite lateral sides of the anterior superior iliac spine (ASIS) to affect bone movement along the sacroiliac joint.

The size and configuration of the expandable segments 30 can vary. In a representative embodiment shown in FIG. 3C, a single, axially elongated expandable segment for the substantially the entire thoracic region is shown, e.g., extending generally from T1 to T11 and measuring, e.g., about 5 to 8 inches wide transverse the axis of the spine and about 20 inches+/−5 inches axially along the axis of the spine. Also, in the representative embodiment shown FIG. 3C, there are a plurality of individual expandable segments 30 in the lumbar region, e.g., extending generally from T12 to T5 and each expandable segment 30 measuring, e.g., about 5 to 8 inches wide transverse the axis of the spine and about 1 to 2 inches along the axis of the spine. In the representative embodiment shown FIG. 3C, there is a single expandable segment for substantially the entire sacral region, measuring about half the size of the expandable segment in the thoracic region. In FIG. 3C, there are also expandable segments 30 carried on the front of the garment 10, in the pantaloon region 18, that register over opposite lateral sides of the anterior superior iliac spine (ASIS) to affect bone movement along the sacroiliac joint. This is also shown in FIG. 12.

Figure 3D:
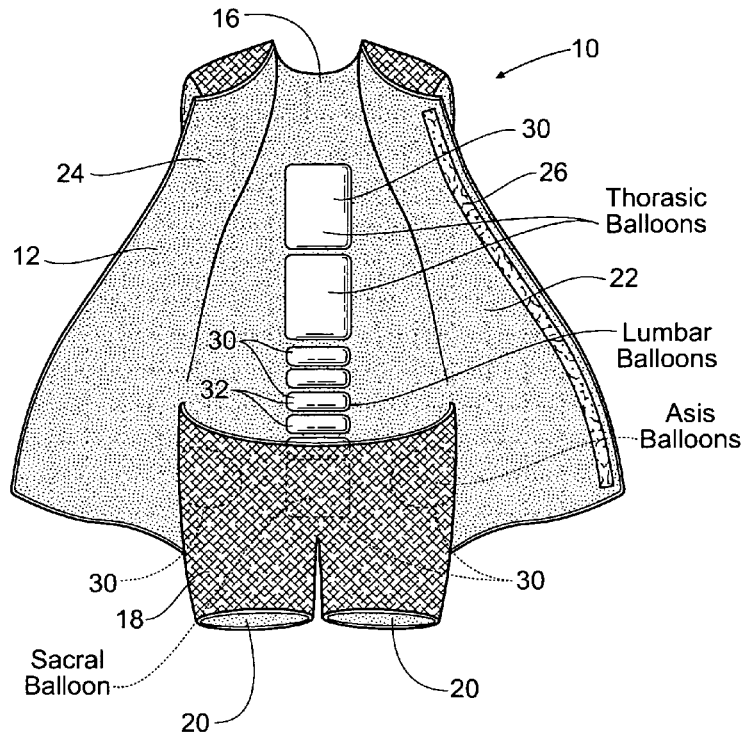
FIGS. 3D and 3E are alternative views of the garment in a fully opened condition, showing alternative arrangements of the series of expandable segments within the garment that are precisely positioned to align, when the garment is worn, with groups of vertebrae or individual vertebrae along the thoracic, lumbar, and sacral regions of the spine, as well as with pelvic bones affecting the sacroiliac joint.
Figure 3E:
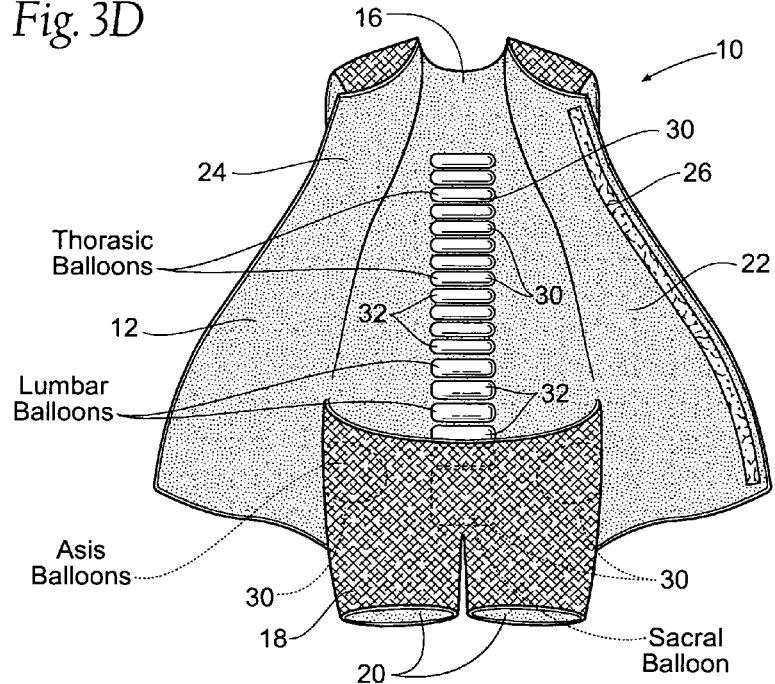

FIGS. 3D and 3E show alternative different illustrative configurations. In FIG. 3D, there are two expandable segments 30 in the thoracic region. In FIG. 3E, there are separate expandable segments 30 for each vertebra in the thoracic and lumbar regions.

The actuators 32 also may take various forms and configuration, depending upon the size and configuration of the expandable segments 30. In the illustrated embodiment of FIGS. 3C, 3D, and 3E, the actuators take the form of inflatable bodies that form or are carried within the expandable segments 30. The expandable bodies can comprise, e.g., balloons made from elastic, non-elastic, or semi-elastic materials. Tubing 40 individually couples each expandable body to a source of expansion air or (desirably) liquid (see FIG. 5) that does not degrade the actuator or interfere with imaging, so that each expandable body can be selectively enlarged or collapsed in a controlled manner by the caregiver, as desired, see FIGS. 6 and 7 show.

Figure 13:
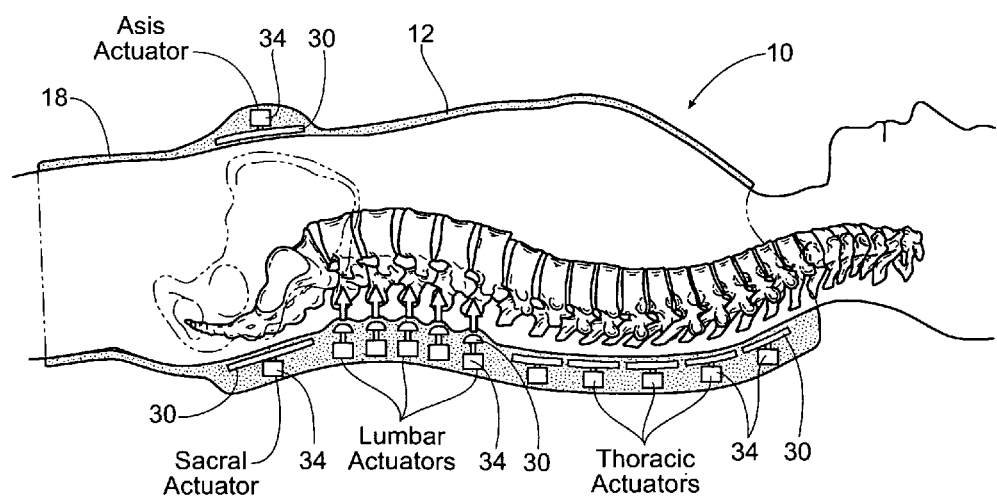
FIG. 13 is a side section view of the individual shown in FIG. 5, showing mechanical actuators carried within the expandable sections, and further showing the selective enlargement of the expandable sections by the mechanical actuators in the lumbar region to simulate extension of the spine during diagnostic imaging.

Alternatively, as shown in FIG. 13, the actuators 32 can take the form of mechanical jack type lifters or small elevators 34 that are carried within the expandable segments 30. The mechanical actuators 34 can selectively and individually be operated to achieve the desired results, as just described.

Figure 14:
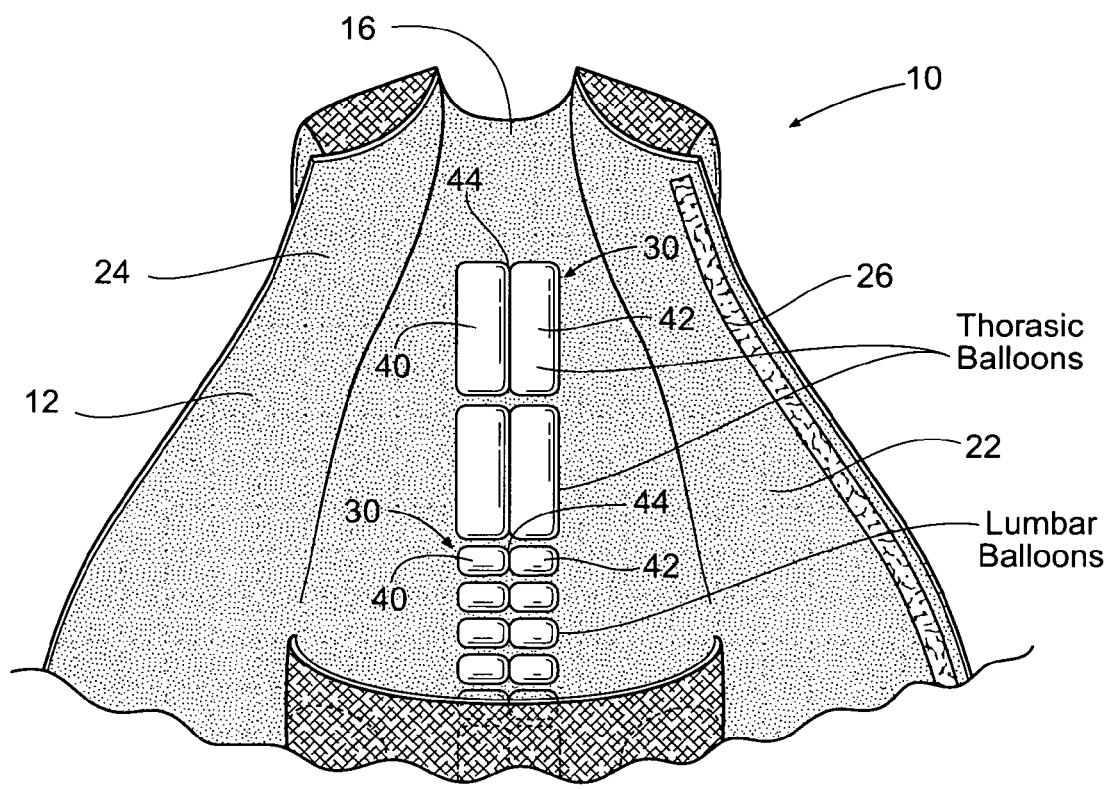
FIG. 14 is a front view of a garment of the type shown in FIG. 3A, with the garment fully opened, to show a series of expandable segments within the garment that are precisely positioned to align, when the garment is worn, with groups of vertebrae or individual vertebrae along the thoracic, lumbar, and sacral regions of the spine, the expandable segments being partitioned into individual left and right expandable chambers that can be independent enlarged on each vertebral level.

In an alternative embodiment (see FIG. 14), the actuators 32 can be sized and configured to enlarge more on one lateral side (left or right) of a vertebral level than another. For example, the balloons 30 at one or more vertebral levels can be formed to preferentially expand more on one lateral side than other, e.g., by the inclusion of individual right and left lateral size chambers 40 and 42 separated by a septum 44. The chambers 40 and 42 are coupled to individual inflation tubing. Inflation of only a right side chamber 40 (and not the left side chamber 42)—or vice versa—press against only the affected side of the adjacent vertebrae of the individual wearing the garment 10. Thus, more precise and preferential ranges of movement can be provided to lead to greater degrees diagnostic accuracy.

C. Use of the Garment

For example, as shown in FIGS. 5 and 6, the individual wearing the garment 10 lays supine on an imaging table 36 in an imaging field 38. Once the individual is positioned for imaging, expandable segments of the garment can be systematically and preferentially enlarged to affect movement of adjacent vertebra. In FIG. 7, all of the expandable segments 30 in the thoracic, lumbar, and sacral regions are enlarged for the purpose of illustration. However, selective groups of some expandable segments 30 can be enlarged, without enlarging other selective groups of the expandable segments 30.

Figure 8:
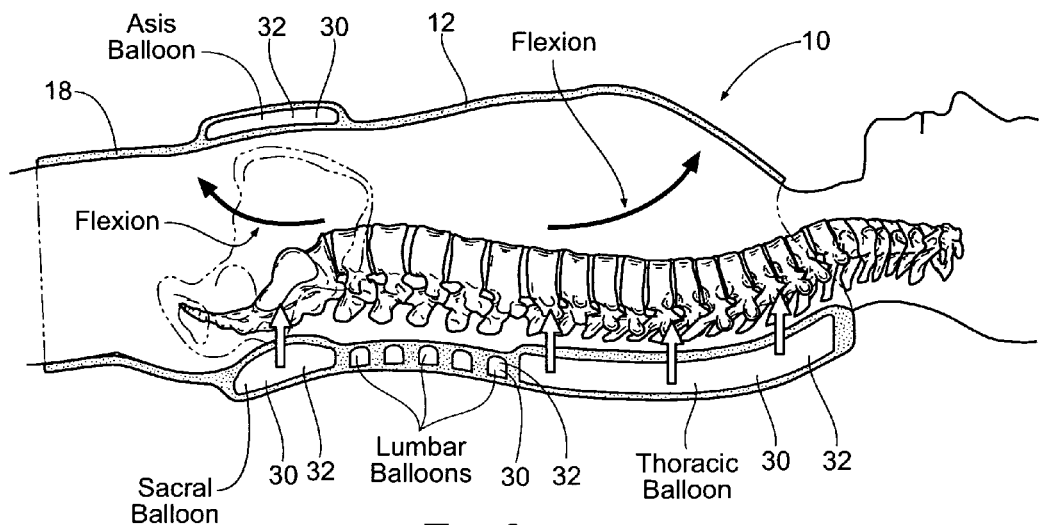
FIG. 8 is a side section view of the individual shown in FIG. 5, showing the selective enlargement of the expandable sections by fluid pressure along the thoracic and sacral regions to simulate flexion of the spine during diagnostic imaging.
Figure 9:
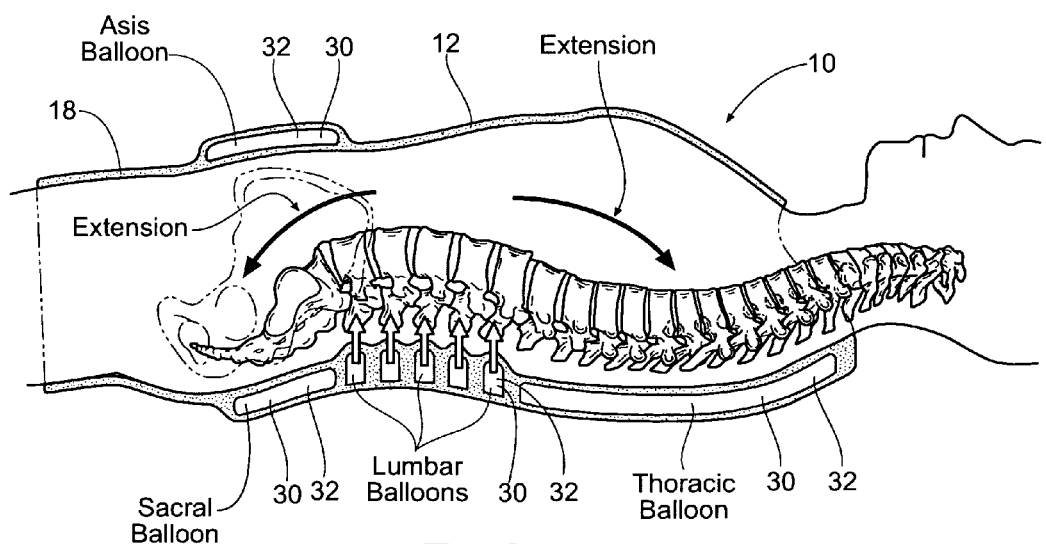
FIG. 9 is a side section view of the individual shown in FIG. 5, showing the selective enlargement of the expandable sections by fluid pressure along the lumbar region to simulate extension of the spine during diagnostic imaging.
Figure 10:
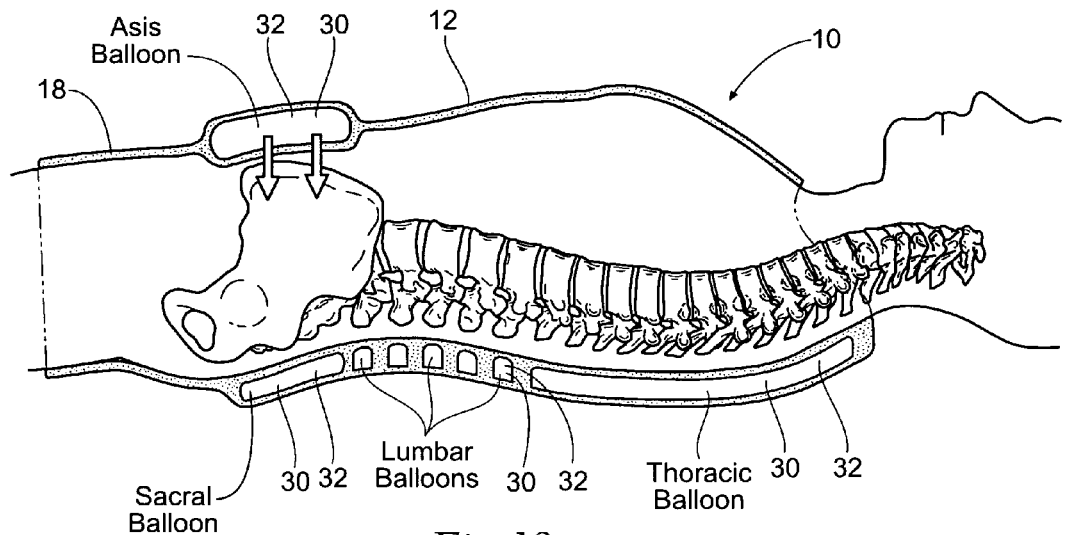
FIGS. 10 and 11 are, respectively, a side section view and a transverse section view of the individual shown in FIG. 5, showing the selective enlargement of the expandable sections over opposite lateral sides of the anterior superior iliac spine (ASIS) to affect bone movement along the sacroiliac joint.
Figure 11:
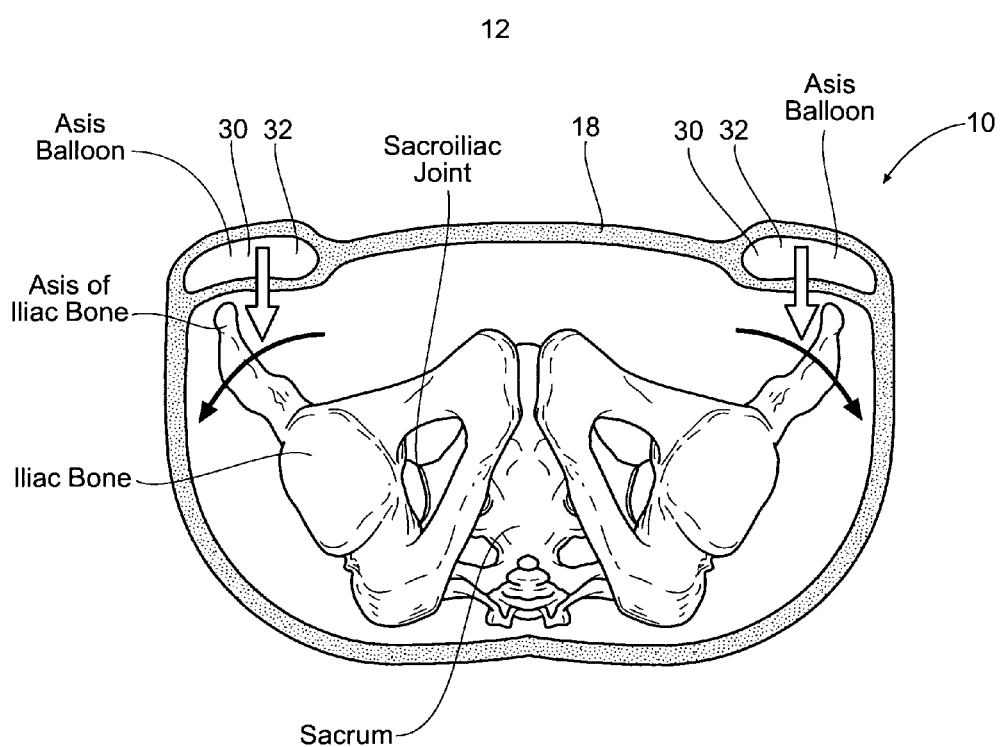

For example, in FIG. 8, only the expandable segments 30 for the thoracic and sacral regions are selectively enlarged (the expandable segments 30 in the lumbar region not being enlarged), to determine what effect simulated flexion may have on back pain and the spine. Or, as shown in FIG. 9, only the expandable segments 30 in the lumbar region can be selectively enlarged (the expandable segments 30 for the thoracic and sacral regions not being enlarged), to determine what effect extension may have on back pain and the spine. To test the sacroiliac joint (as FIGS. 10 and 11 show), both expandable segments 30 on the ASIS can be enlarged, along with the expandable segment for the sacral region (if desired), to stress the sacroiliac joint from two directions.

Once an incident of back pain is generated, the incident of pain can be correlated to the orientation of the spine that is captured by the imaging at the time the pain occurs. In this way, the orientation and motion of the spine that causes back pain can be systematically simulated and examined, to identify which movement of particular bone or bones, or which orientation of the spine, causes the back pain.

The garment 10 can also be used as a diagnostic tool in and of itself, without the use of imaging. For example, by enlarging both expandable segments 30 on the ASIS along with the expandable segment 30 for the sacral region, the sacroiliac joint can be stressed from two directions. If the sacroiliac joint is a pain generator when stressed in this manner, this alone can serve as a diagnosis of dysfunction at the sacroiliac joint.

Other embodiments and uses of the inventions described herein will be apparent to those skilled in the art from consideration of the specification and practice of the inventions disclosed. All documents referenced herein are specifically and entirely incorporated by reference. The specification should be considered exemplary only with the true scope and spirit of the invention indicated by the following claims. As will be easily understood by those of ordinary skill in the art, variations and modifications of each of the disclosed embodiments can be easily made within the scope of this invention as defined by the following claims.

I claim:

1. A method for diagnosis of an underlying cause of back pain in an individual comprising
   identifying an individual experiencing back pain,
   fitting a garment on the individual, the garment including a series of expandable segments configured to overlay groups of vertebrae along sacral region of the individual's spine and over opposite lateral sides of the anterior superior iliac spine, the garment including an array of actuators carried within the expandable segments that can be controllably enlarged to press against adjacent bone structures to move and orient vertebrae, muscles, and nerves of the spine, the garment, expandable segments, and actuators being made of material that does not substantially interfere with diagnostic imaging,
   placing the individual wearing the garment in an imaging field,
   operating the actuators to enlarge the expandable segments overlying the sacral region and the opposite lateral sides of the anterior superior iliac spine to stress the sacroiliac joint from two directions,
   diagnostically imaging the spine during operation of the actuators,
   observing an incident of back pain during operation of the actuators, and
   correlating the incident of back pain to the diagnostic image to diagnose an underlying cause of back pain in the individual by identifying one or more movements of particular bone or bones and which orientation of the spine causes the back pain.

2. The method of claim 1, wherein the garment further includes a series of expandable segments configured to overlay groups of vertebrae along the lumbar and thoracic regions of the spine.

3. The method of claim 2, wherein the garment further comprises a pantaloon region that is configured to be worn around the waist and hips of the individual.

4. The method of claim 1, wherein the garment further comprises a vest region that is configured to be worn on the upper torso of the individual.

5. The method of claim 1, wherein the garment further comprises a removable inner garment made of material that does not substantially interfere with diagnostic imaging.

6. The method of claim 1, wherein the actuators are inflatable bodies.

7. The method of claim 1, wherein the actuators are mechanical jack type lifters.

8. A method for diagnosis of an underlying cause of back pain in an individual comprising identifying an individual experiencing back pain, fitting a garment on the individual, the garment including a series of expandable segments configured to overlay groups of vertebrae along the lumbar region and sacral region of the individual's spine and over opposite lateral sides of the anterior superior iliac spine, the garment including an array of actuators carried within the expandable segments that can be controllably enlarged to press against adjacent vertebrae to move and orient vertebrae, muscles, and nerves of the spine, the garment, expandable segments, and actuators being made of material that does not substantially interfere with diagnostic imaging, placing the individual wearing the garment in an imaging field, operating the actuators to enlarge the expandable segments overlying one or more of the lumbar region and sacral region and operating the actuators to enlarge the expandable segments overlying the opposite lateral sides of the anterior superior iliac spine, diagnostically imaging the spine during the operation of the actuators, observing an incident of back pain during the operation of the actuators, and correlating the incident of back pain to the diagnostic image to diagnose an underlying cause of back pain in the individual by identifying one or more movements of particular bone or bones and which orientation of the spine causes the back pain.

9. The method of claim 8, wherein the garment further includes a series of expandable segments configured to overlay one or more posterior portions of pelvic bones affecting the sacroiliac joint.

10. The method of claim 9, further comprising operating the actuators to enlarge the expandable segments configured to overlay one or more of the lumbar region, the sacral region, and the one or more posterior portions of pelvic bones affecting the sacroiliac joint.

* * * * *